United States Patent
McKinnon et al.

(10) Patent No.: US 8,616,200 B2
(45) Date of Patent: Dec. 31, 2013

(54) RESERVOIR SYSTEM FOR GAS DELIVERY TO A PATIENT

(75) Inventors: Robert J. McKinnon, Highlands Ranch, CO (US); James Dale Bickley, Tucson, AZ (US)

(73) Assignee: Westmed, Inc., Greenwood Village, CO (US)

( * ) Notice: Subject to any disclaimer, the term of this patent is extended or adjusted under 35 U.S.C. 154(b) by 659 days.

(21) Appl. No.: 12/688,295

(22) Filed: Jan. 15, 2010

(65) Prior Publication Data

US 2010/0180891 A1  Jul. 22, 2010

Related U.S. Application Data

(60) Provisional application No. 61/145,318, filed on Jan. 16, 2009.

(51) Int. Cl.
*A61M 15/00* (2006.01)

(52) U.S. Cl.
USPC ........................................... 128/203.12

(58) Field of Classification Search
USPC ............. 128/205.13, 203.12, 203.28, 205.11, 128/205.24, 204.29, 200.14, 200.16
See application file for complete search history.

(56) References Cited

U.S. PATENT DOCUMENTS

| | | | |
|---|---|---|---|
| 3,906,996 A | | 9/1975 | DePass et al. |
| 3,967,619 A | | 7/1976 | Story et al. |
| 4,088,131 A | | 5/1978 | Elam et al. |
| 4,676,239 A | | 6/1987 | Humphrey |
| 4,823,784 A | | 4/1989 | Bordoni et al. |
| 5,020,530 A | | 6/1991 | Miller |
| 5,061,241 A | * | 10/1991 | Stephens et al. ............. 604/114 |
| 5,099,833 A | | 3/1992 | Michaels |
| 5,613,489 A | * | 3/1997 | Miller et al. ............. 128/203.28 |
| 2011/0277754 A1 | | 11/2011 | McKinnon et al. |

FOREIGN PATENT DOCUMENTS

GB  293900  7/1928

\* cited by examiner

*Primary Examiner* — Manuel Mendez
(74) *Attorney, Agent, or Firm* — Sheridan Ross P.C.

(57) ABSTRACT

An oxygen delivery system is provided that employs a reservoir for holding oxygen or an oxygen and medicine mixture while the patient is not inhaling. The reservoir generally prevents waste and reduces cost and helps prevent the patient from re-inhaling the previously exhaled gases.

9 Claims, 5 Drawing Sheets

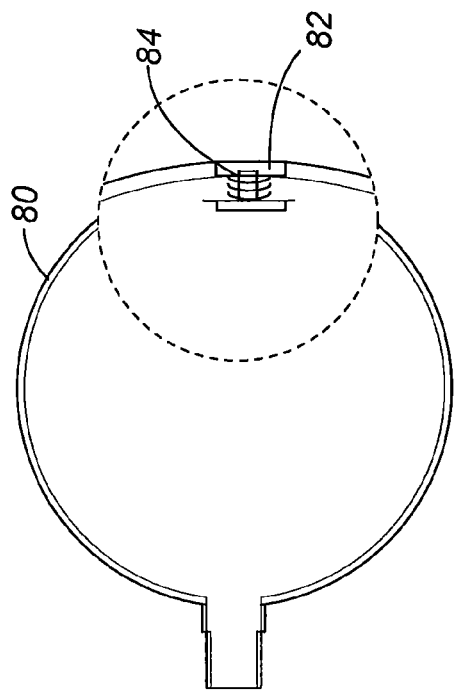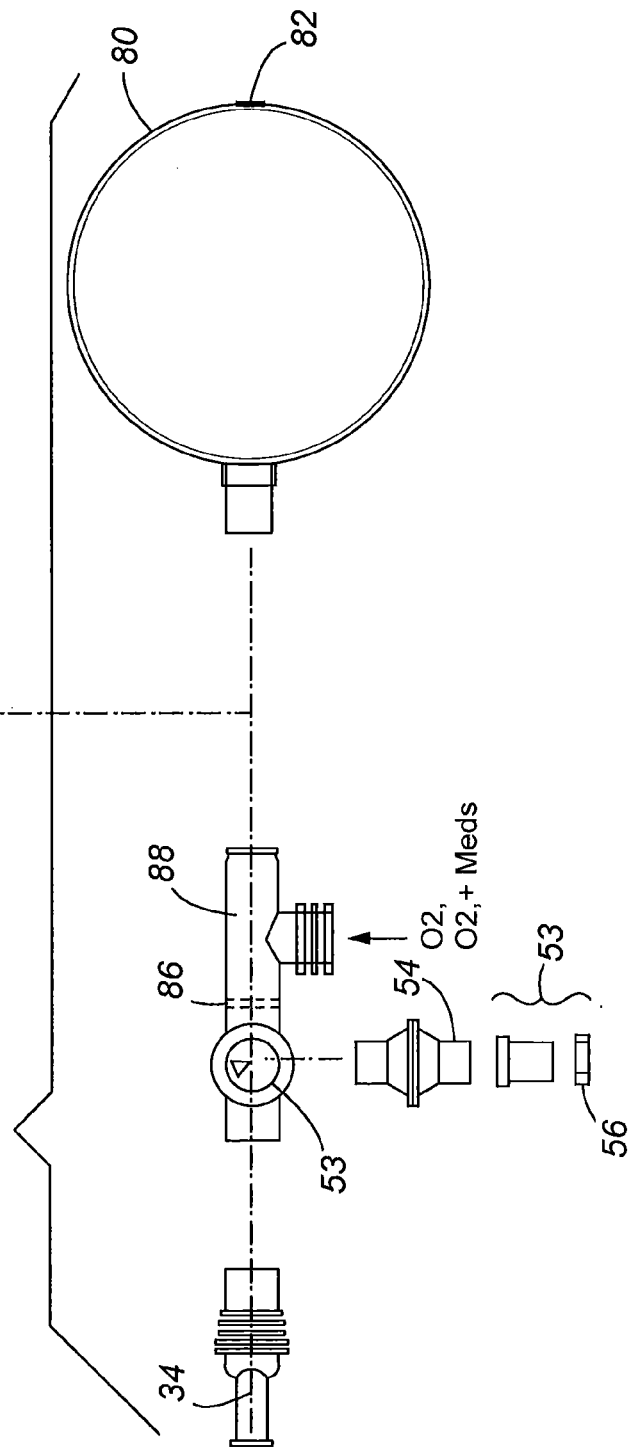

RESERVOIR SYSTEM FOR GAS DELIVERY TO A PATIENT

CROSS-REFERENCE TO RELATED APPLICATION

Figure 1:
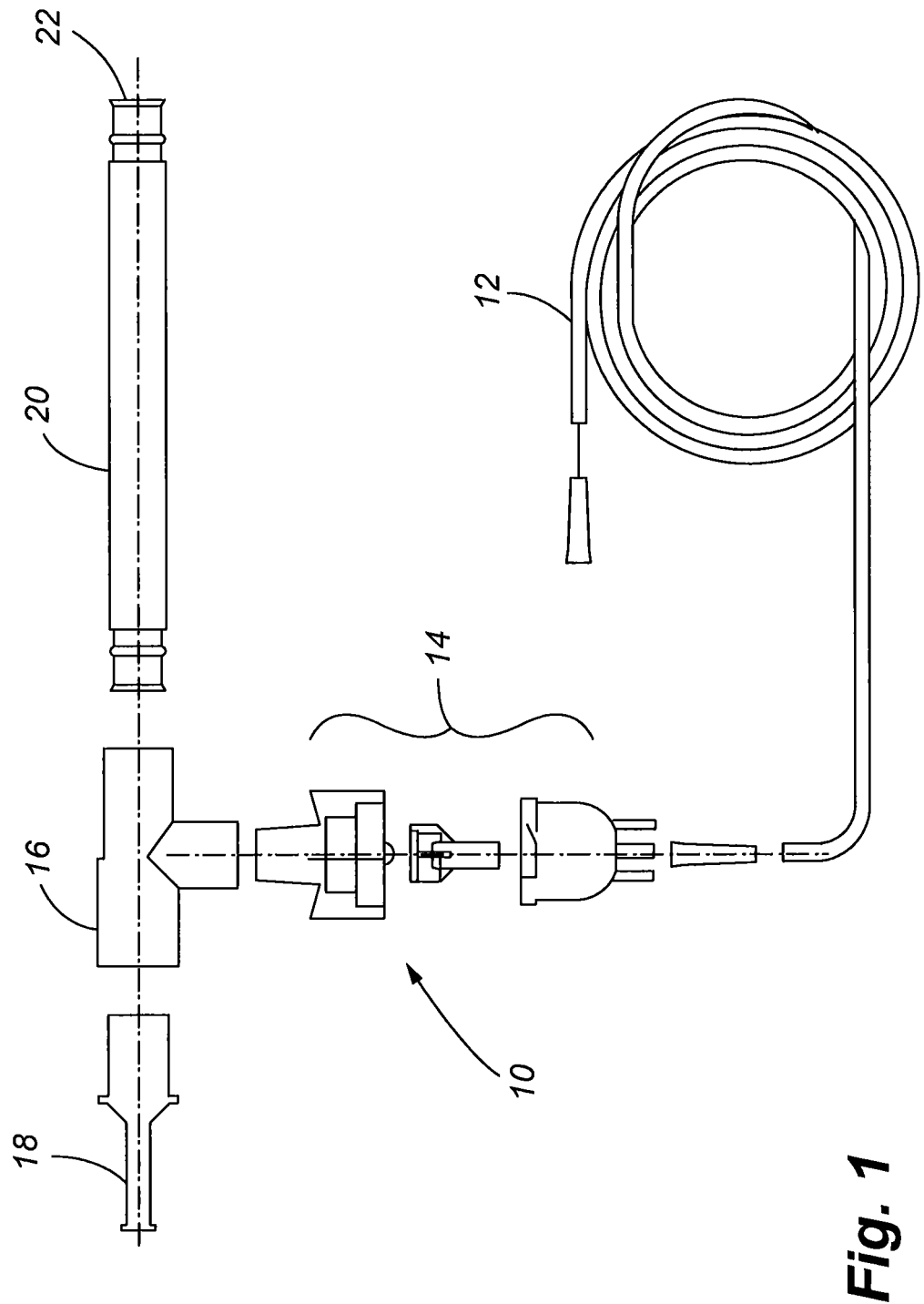

The present application claims the benefit of U.S. Provisional Application Ser. No. 61/145,318 filed Jan. 16, 2009 entitled "Reservoir System for Oxygen and Medicine Delivery to a Patient," the entirety of which is incorporated herein by this reference.

FIELD OF THE INVENTION

The invention relates to a reservoir system designed to provide gas, such as oxygen or an oxygen and medicine mixture, to a patient.

BACKGROUND OF THE INVENTION

Gas is typically delivered to a patient by systems that generally include a source, a mouth piece or mask and tubing interconnecting these components. "Gas" as used herein is comprised of compressed air, oxygen, helium and oxygen, a mixture of oxygen and medicine, or any other gas that would typically be used for patient care, etc. The following specification is focused on oxygen or an oxygen/medicine mixture, which will be described in detail below, the use of "oxygen" is thus for example only and does not limit the scope of the contemplated invention. To avoid a patient rebreathing his or her exhalation and, thus not receiving a fresh or sufficient supply of oxygen and/or medicine, gas delivery systems may also include a one-way valve to prevent exhaled air from mixing with the incoming supply of oxygen or aerosol mixture. The pressure generated by the patient's exhalation is sufficient to close the valve such that the exhalation vents through an outlet port. The pressure generated by the patient's inhalation is sufficient to open the valve, allowing the patient to breath in the prescribed oxygen or aerosol mixture.

Typically the oxygen source continuously outputs oxygen at a predetermined but variable rate or pressure. When the patient is not inhaling, oxygen continues to be delivered wherein the excess oxygen is vented to atmosphere through the outlet port and/or through the mouth piece. Medicine may also be delivered to a patient through a similar delivery system. For example, a nebulizer may be added to the oxygen delivery system such that liquid medicine is aerosolized and mixed with the oxygen flow. A nebulizer may also be used with a system that uses ambient air, rather than oxygen, as the carrier for the aerosolized medicine. In either case, the same problem of waste exists. That is, when the patient is not inhaling, the aerosolized medicine continues to be supplied by the oxygen source and the mixture (medicine plus ambient air and/or oxygen) is vented to the atmosphere. To account for the loss of medicine, health care providers typically over prescribe medicine delivered by this method. Generally, a patient's inhalation accounts for approximately one-third of the breathing cycle, with the remaining two-thirds being exhalation and dwell time. Thus, three times the required dosage may be prescribed to accommodate system losses, which is wasteful and increases health care costs.

One attempt to solve the problem of waste has been to add a reservoir bag to the delivery system. The intended purpose of a reservoir bag is to capture the oxygen and/or aerosolized medicine that is delivered during those time periods when a patient is not inhaling, rather than vent it into the atmosphere. When the patient does inhale, it is intended that the oxygen and/or aerosolized medicine stored in the reservoir bag is available to be inhaled, together with the oxygen and/or aerosolized medicine that is being continuously output from the supply source. Accordingly, it is intended that less oxygen and/or aerosolized medicine is wasted and there is an available reserve of oxygen and/or aerosolized medicine in the reservoir bag for the patient to inhale when the inhalation process starts.

Often reservoir bags are constructed of relatively thick walls and material to provide durability to withstand damage in shipping, handling and use. Due to the thick walled construction, the reservoir bag does not inflate well, if at all. More specifically, as the pressure required to inflate a thick walled bag is greater than the pressure required to open the previously-discussed one-way valve, the pressurized oxygen will seek the path of least resistance and will be fed to the mask and ultimately wasted. That is, the one-way valve opens without the reservoir bag being filled and the oxygen and/or medicine is vented to atmosphere through the outlet port rather than filling the reservoir. One ineffective response to this problem is to increase the pressure of the oxygen or aerosol delivery which would ideally inflate the bag. However, if the initial, lower pressure is sufficient to open the one-way valve, increasing the pressure will have the same effect. Even if the reservoir bag opens as a result of the increase in pressure, once the one-way valve is open, the oxygen or aerosol mixture will vent to atmosphere instead of filling the reservoir. Moreover, increasing the pressure of the system results in a greater flow rate of the oxygen and/or aerosolized medicine which means more oxygen and/or aerosolized medicine will be lost through the outlet port than when the system was operating at a lower pressure. Another way to address this drawback is to reduce the size of the opening of the outlet port. Applicant owns U.S. Pat. No. 5,613,489 directed to an outlet port valve with an adjustably sized opening, the entirety of which is incorporated herein by reference. However, even if the outlet port is reduced in size, the one-way valve will inevitably open to allow oxygen or aerosol to escape through the outlet port.

Accordingly, there is a long standing and unresolved need to provide a reservoir system for use with an oxygen or aerosol delivery system whereby a reserve of oxygen or an aerosolized medicine mixture is created in a reservoir when the patient is not inhaling, thereby eliminating or substantially reducing the waste of medicine and/or oxygen and ensuring the patient receives the prescribed dosage of each—without harming the patient.

SUMMARY OF THE INVENTION

Embodiments of the present invention provide a gas delivery system with a reservoir wherein internal system pressure requirements are established to cause the reservoir to fill or substantially fill while the patient is not inhaling. More specifically, one embodiment of the present invention employs a one-way valve with increased resistance. Further, resistance may be added to the system, such as by placing a filter, a throttle; decreased diameter tubing, or some other medically inert porous obstruction upstream of the outlet port. As used herein, "upstream" refers to a position closer to the gas supply and away from the patient. Still further, if an inflatable reservoir is used, the thickness of the walls of the inflatable reservoir may be reduced. Each of these solutions, alone or in combination, will cause the reservoir bag to inflate and fill with oxygen and/or a mixture of oxygen/medicine such that a reserve is available for the patient, which will reduce waste. In one embodiment, the resistance to gas flow occurs before the gas reaches the outlet port of the delivery system. In other words, any structure or component added, altered or selectively altered for purposes of increasing the internal resistance to gas flow toward the outlet port must not be positioned between the patient mouth piece and the outlet port, otherwise the solution will be ineffective as the oxygen or aerosol will vent to atmosphere through the outlet port. Additionally, the internal system pressure may be adjusted relative to the volume and rate of the patient's breath cycle such that the reservoir fills or is substantially filled prior to each inhalation cycle.

FIG. 1 is an example of a current commercial aerosol delivery system 10 that does not employ a reservoir bag or one-way valving system. Oxygen or ambient air flows though supply tubing 12 and the nebulizer 14 and the resulting aerosol mixture travels through housing 16 and mouth piece 18 toward the patient, into tubing 20 or both, depending upon the dynamic internal system pressures. The mouth piece 18 may be replaced by a mask 14 as shown in FIG. 4. The tubing 20 may act as a reservoir wherein inhalation will draw gas from the tube 20, through the housing 16 and to the mouth piece 18. The inhaled gas thus comprises the aerosol mixture from the nebulizer 14 and whatever gas is resident in the tubing 20. On exhalation, the exhaled gases flow out through the mouth piece 18 and housing 16 into the tubing 20 and ultimately into atmosphere through outlet port 22 of the tubing 20. During any period of time when the patient is not inhaling, the aerosol mixture from the nebulizer 14 will flow toward the mouth piece 18 and toward the outlet port 22. The portion of the aerosol mixture that flows toward the outlet port 22 will purge at least some of the exhaled $CO_2$ that may be reside in the tubing 20. However, if adequate flow sufficient to achieve a complete purge of $CO_2$ from the tubing 20 is not provided, the patient may re-breathe the $CO_2$ residing in the tubing 20 upon subsequent inhalation. In addition, using the aerosol mixture for purging exhalation gases wastes medication and reduces the prescribed volume of medication that is directed to the patient, thereby requiring the dosage to be increased.

BRIEF DESCRIPTION OF THE DRAWINGS

FIG. 1 shows an exploded view of one embodiment of a currently available commercial gas delivery system, including a nebulizer.

FIG. 2 shows an exploded view of a first embodiment of the present invention, including a nebulizer.

FIG. 3 shows a housing employed by some embodiments of the present invention.

FIG. 4 shows an exploded view of an alternative embodiment of the present invention, without a nebulizer.

FIG. 5 shows an exploded view of a further alternative embodiment of the present invention.

FIG. 6 shows an enlargement of a non-inflatable reservoir with a one-way valve.

While the following disclosure describes the invention in connection with those embodiments presented, one should understand that the invention is not strictly limited to these embodiments. Furthermore, one should understand that the drawings are not necessarily to scale, and that in certain instances, the disclosure may not include details that are not necessary for an understanding of the present invention, such as conventional details of fabrication and assembly.

DETAILED DESCRIPTION

Turning to FIGS. 2 and 3, a pulmonary drug delivery system 30 is shown. In general terms, the pulmonary drug delivery system 30 comprises a main housing 32, a patient interface port 33, such as a mouth piece 34, associated with the main housing 32, an reservoir port 36 associated with the main housing 32, a nebulizer 38 associated with the main housing 32, a gas source 40 associated with the nebulizer 38 and connected thereto by appropriate tubing 42, and an inflatable/deflatable reservoir 44 associated with the main housing. The gas source 40 may be an oxygen tank, the hospital's oxygen source, a blender that is connected to a combination of gas sources, an oxygen concentrator, a compressor, for example. For illustrative purposes, the gas source will be an oxygen source for the following description. A connector 46 may be used to interconnect the reservoir 44 to the main housing 32, and a band 48 or tape provides one option of sealing the reservoir 44 to the connector 46. An oxygen line 42 is attached between the nebulizer 38 and the source of oxygen or ambient air 40 and supplies the nebulizer which causes medication positioned in the nebulizer to be aerosolized and mixed with the oxygen or air for inhalation by the patient. As used herein, the term "aerosolized mixture" will refer to a mixture of medicine and oxygen and/or air. A one-way valve 50 is installed in the main housing 32. A seat (see FIG. 3, #51) may be formed in the housing 32 upon which the valve 50 is positioned. The valve 50 allows fluid, e.g., air, oxygen or an aerosolized mixture to flow to the patient through the mouth piece 34 but restricts exhaled air to flow into the nebulizer 38 or the inflatable reservoir 44. The valve 50 should be open for the oxygen or aerosolized mixture to travel to the mouth piece 34.

The flow rate at which oxygen or air is supplied to the nebulizer is a known amount and may be adjusted as required. In one embodiment, the pressure being delivered by the source is greater than the pressure required to open the one-way valve 50, but the flow rate of the pressurized oxygen or aerosolized mixture is decreased so that it takes some time for the pressure in the reservoir 44 and housing 32 to reach a level that would open the valve 50. Accordingly, when a patient is not inhaling, the oxygen or aerosolized mixture exiting nebulizer 38 will accumulate in the reservoir. At some point, however, the valve 50 will open due to the pressure build up in the housing 32 and the reservoir 44. If the patient is not inhaling at this time, the excess oxygen or aerosolized mixture will vent. Upon inhalation, the valve will open or remain open and allow the patient to receive the aerosolized mixture or oxygen from the nebulizer 38, as well as the supply of aerosolized mixture or oxygen contained in the reservoir 44.

The flow rate of the aerosolized mixture or oxygen from the nebulizer 38 should be adjusted to correspond with the patient's inhalation such that the volume of aerosolized mixture or oxygen that accumulates in the reservoir matches or nearly matches the patient's inhalation volume intake, accounting for the volume of oxygen or aerosolized mixture that would also be simultaneously supplied from the nebulizer or oxygen source. Should the patient over-breathe and deplete the volume of aerosolized mixture or oxygen in the reservoir, the patient may still inhale the aerosolized mixture being generated by the nebulizer as well as ambient air drawn through an outlet 52 or Positive Expiratory Pressure (PEP) valve 53. When the patient exhales, the one-way valve will close and all exhaled gas will exit through the PEP valve 53. One of skill in the art will appreciate that the exhaled gas may exit though another outlet integrated into the housing 32, the mouth piece 34, the mask (if applicable), etc. That is, the PEP valve is not necessarily required for the contemplated invention to function. The PEP valve may employ a member 56 that is selectively rotated to control the flow of fluid therethrough. In one embodiment the PEP valve 53 is used in conjunction with a filter mechanism 54 to filter exhaled gases, remove contaminants, bacteria, viruses and other contaminates for the safety of healthcare workers and others attending to the needs of the patient. During exhalation and any pause prior to the next inhalation, the aerosolized mixture or oxygen will inflate the reservoir 44.

To insure that the reservoir 44 fills, even in the case of patients requiring high flow rates, which requires higher internal pressures could cause the one-way valve 50 to open prematurely, the resistance of the valve 50 may be increased. In one embodiment, a manually adjustable spring is used to alter the resistance of the valve 50. Alternatively, the one-way valve of increased resistance (not shown) may be placed in the delivery system upstream of the PEP valve 53, i.e., between the PEP vale 53 and one-way valve 50. This second valve would compensate an unintended opening of valve 50. Further, resistance could take the form of one or more filters, some type of inert or non-harmful but porous obstruction, a throttle in the tubing, a throttle in the housing 32, a tortuous air path, a flow path comprising flexible walls that expand and contract with pressure changes, tubing with integrated pressure relief characteristics (i.e., a hole covered by a flexible member that allows gas to escape when the pressure of the gas reaches a predetermined level), or a combination of one or more of these options. An important feature is that the internal resistance to gas flow toward the mouth piece upstream of the PEP valve 53 is greater than that required to fill the reservoir bag 44.

Figure 3:
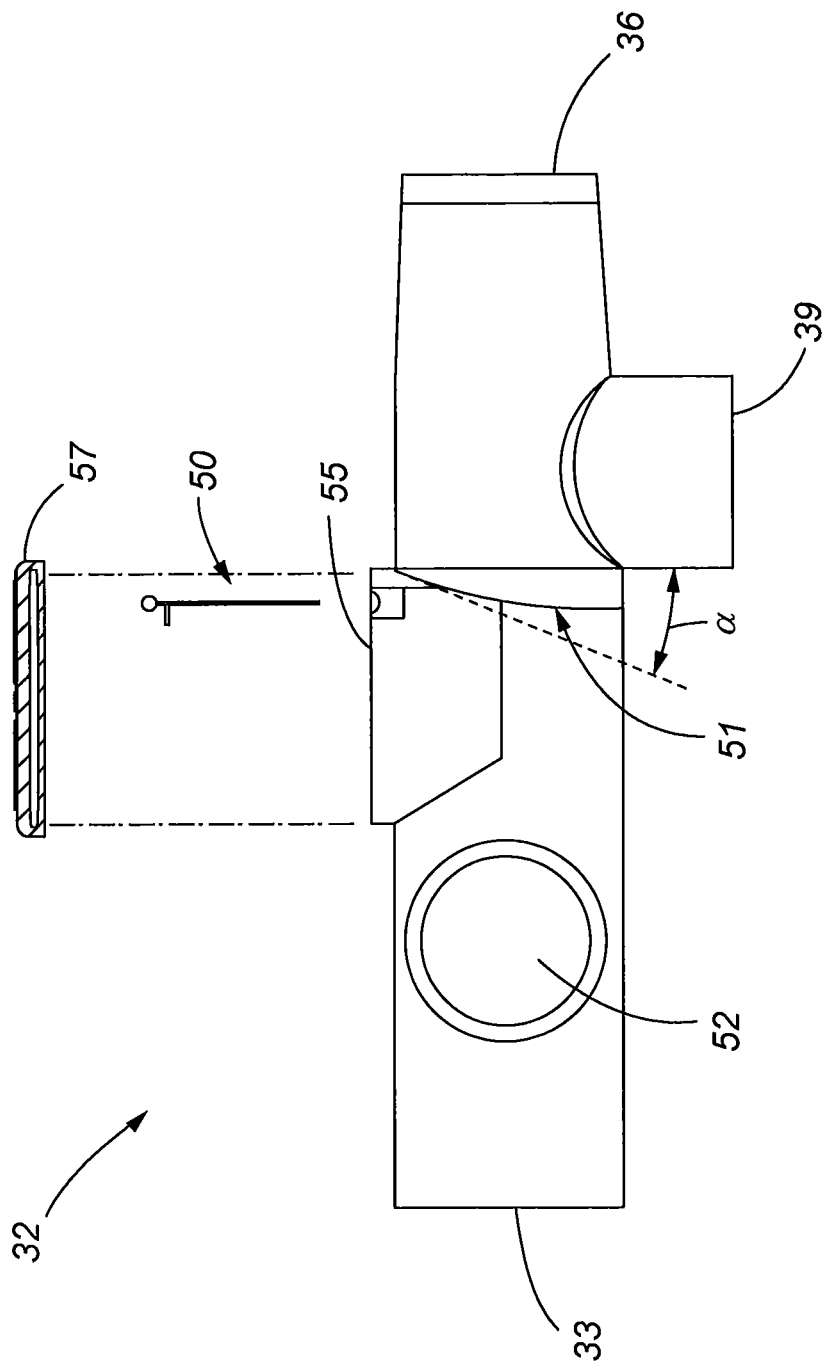

Referring now to FIG. 3, the housing 32 of one embodiment of the present invention is shown that includes a patient interface port 33, a nebulizer port 39 and a reservoir port 36. The housing 32 also includes the outlet 52 that is adapted to interconnect with the PEP device. The valve 50 is integrated into the housing 32 via an opening 55 in a portion of the housing 32. A cap 57 is also integrated to the opening to seal the housing 32. The valve 50 rests against a valve seat 51, which may be angled (α). The valve seat 51 will alter the pressure required to open the valve 50 as a function of angle (α). More specifically, if the valve is positioned vertically as shown, it will require less pressure to open if it is angled, for example, about 30 degrees, wherein the weight of the valve 50 must be additionally overcome to open the same.

Figure 4:
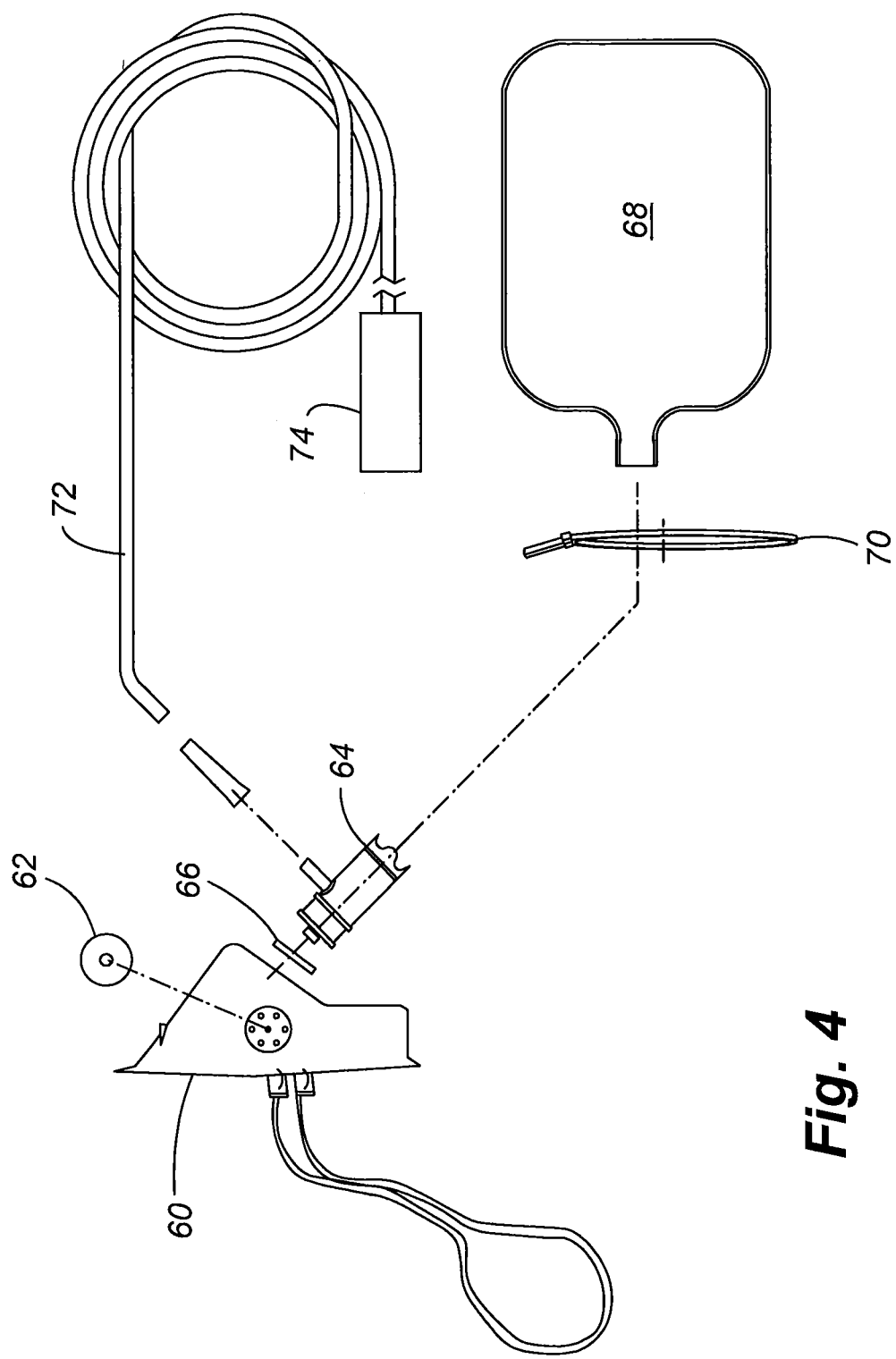

FIG. 4 illustrates a non re-breather mask system incorporating an embodiment of the present invention. A patient mask 60 may have one or more one-way valves 62 to prevent or control inhalation of ambient air. Alternatively, the mask 60 may have exit vents that are not valves or the exhalation may simply escape around the peripheral edges of the mask. A housing 64 is provided with a one-way valve 66 installed to prevent exhaled gas from entering the housing 64. A reservoir bag 68 may be attached to the housing 64 with an attaching device 70 such as a band tie or tape. The housing 64 also is interconnected to an oxygen line 72 that is also associated with an oxygen or ambient air source 74.

When the oxygen source is turned on, pressurized oxygen will fill the reservoir bag 68 until the patient inhales. On inhalation, the valve 66 opens and valve(s) 62 close causing all of the inhaled gases to come from the oxygen supply 74 and/or the reservoir 68. The flow of oxygen may be adjusted to meet the patient's requirements. On exhalation, valve 66 closes and valve(s) 62 open to allow the exhaled gas to escape from the mask and the reservoir bag 68 to refill with oxygen. A nebulizer (not shown) may be added between the housing 64 and the oxygen supply line 72 and the system will work in the same way but the reservoir and patient will be provided with an aerosolized mixture of oxygen and medicine or ambient air and medicine.

With the current state of the art non-re-breather mask systems, the reservoir bag is stiff, as described above, and in order to fill the reservoir bag when the patient is not inhaling the pressure from the oxygen supply must be increased. However, the increased pressure also causes valves 62 and 66 to open causing at least some of the oxygen or aerosol mixture to exit out to atmosphere when the patient is not inhaling. Oxygen or aerosol mixture is thus wasted and the quantity of medicine or oxygen must be increased to accommodate the loss and to ensure the patient receives the prescribed amount of medicine.

In one embodiment of the present invention the pressure required to open valve(s) 62 and 66 is adjusted to require a pressure greater than the pressure required to substantially fill the reservoir 68 but is less than the pressure needed to open the valve 66 when the patient inhales. This assures the patient receives the prescribed oxygen level, requires less oxygen flow to achieve the prescribed oxygen levels and reduces or eliminates the loss of oxygen or the aerosol mixture. The system of FIG. 4 may also utilize the methods for adjusting system pressures described above in connection with FIG. 2.

Figure 2:
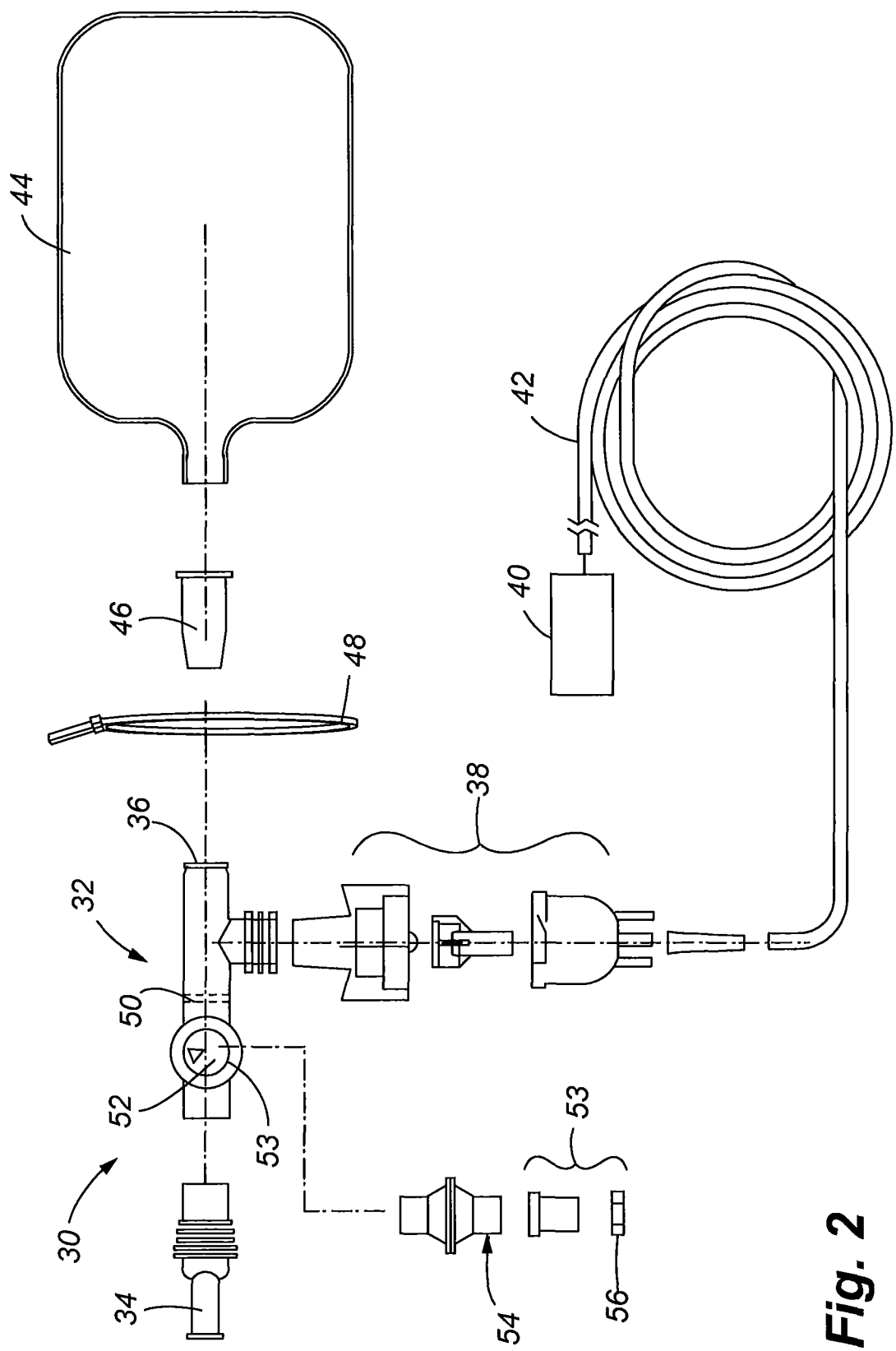

Turning to FIGS. 4-6, a further embodiment of the present invention is provided wherein the inflatable/deflatable reservoir shown in FIGS. 2 and 4 is replaced with a rigid reservoir 80. Although this reservoir is primarily intended for home or residential use, it can be used in any environment, including hospitals, nursing homes and other institutions. The rigid reservoir 80 has the advantage of being more easily washed, cleaned and reused than an inflatable and deflatable reservoir.

In one embodiment, the rigid reservoir 80 includes an opening 82 at its base (on the right hand side as shown in FIG. 5). The opening 82 permits ambient air to be drawn into the reservoir. Similarly, if the main housing is not provided with a one-way valve of the type shown in FIGS. 2 and 3, then the opening 82 may also act as an exit port when a patient is not inhaling. Accordingly, as the source of oxygen or aerosolized mixture is filling the reservoir, the exit hole 82 permits any volume of gas within the reservoir to be purged through the exit hole 82.

Alternatively, as shown in FIG. 6, a one-way valve 84 may be placed at the opening 82 of the rigid reservoir 80 to permit the introduction of ambient air into the reservoir in an overbreathe situation and to preclude aerosolized mixture or oxygen from exiting from the reservoir. More specifically, a spring-biased valve is provided that is normally closed, i.e., the reservoir is closed, wherein the aerosolized mixture cannot escape from the reservoir 80. When the valve 84 is closed, however, the gas will vent through the PEP valve 53 and the reservoir 80 will fill slowly. As the patient inhales and the pressure in the reservoir 80 reduces, the spring force will be overcome and the valve 84 will open to let ambient air into the reservoir 80. During exhalation or dwell, the valve 84 will close to allow the reservoir 80 to fill: In this situation, it may also be desirable to place a one-way valve 86 in the main housing 88 or associated with the patient mouth piece, for example as shown in FIG. 3, such that exhaled air does not enter and contaminate the main housing 88 and reservoir 80. As previously stated, the supply of oxygen and/or aerosolized mixture may be adjusted by adjusting the flow of oxygen from the associated oxygen source. The rigid reservoir may be blow-molded or manufactured in other ways known to those skilled in the art from plastic such as polyethylene, polyvinylchloride (PVC) or flexible PVC.

Although the foregoing discussion concerning FIGS. 4-6 are directed to a rigid reservoir, other embodiments of the present invention employ a semi-rigid, i.e., flexible reservoir. For example, the reservoir may be comprised at least partially of a material that reacts to a negative pressure associated with inhalation but maintains a predetermined shape when not exposed to a pressure variation. This "self-inflating" reservoir will thus return to its static shape in the absence of external or internal pressure, similar to the bulb of a turkey baster, an eyedropper, an aspirator, etc. The material of manufacture of the contemplated reservoir is any number of flexible plastics, for example, flexible PVC of a relatively thin wall thickness in the range of 0.005-0.015 inches. As one of skill in the art will appreciate the contemplated wall thickness would require adjustment depending on the material used. That is, the thicker the material the more memory the part would have but the less likely it would deflate on inhalation. In addition, if the wall thickness is too thin it would not have enough rigidity to be self inflating. One of skill in the art will appreciate that the reservoir can be substantially rigid with a flexible portion, or a bellows, that allows expansion or contraction in response to patient breathing.

The contemplated reservoir would facilitate cleaning thereof as it will substantially maintain its shape when disconnected from the system as the opening associated therewith may be oriented to allow drainage of cleaning fluid. This aspect has an advantage over a substantially collapsible, less rigid bag that would prevent the escape of moisture, thereby promoting bacteria and or mold growth which reduces the life expectancy thereof.

The present invention, in various embodiments, includes components, methods, processes, systems and/or apparatus substantially as depicted and described herein, including various embodiments, sub combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. The features of the embodiments of the invention may be combined in alternate embodiments other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations, combinations, and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. In a gas delivery system for supplementing the breathing of a patient, a system comprising a patient interface device, a source of pressurized gas, a conduit for transporting gas from the source to the mouth piece, an exhalation port disposed proximate the mouth piece and in fluid communication with at least one of the mask and the conduit, and an inflatable reservoir in communication with the conduit between the gas source and the exhalation port, the improvement comprising:
   a one-way check valve positioned in a conduit between said inflatable bag and said exhalation port that creates resistance to gas flow between said inflatable reservoir and said exhalation port that is greater than the resistance associated with filling said inflatable reservoir with gas, said check valve associated with a valve seat that is angled with respect to the longitudinal axis of said conduit between said inflatable bag and said exhalation port.

2. The system of claim 1, further comprising a spring associated with said one-way valve for changing the resistance of the valve.

3. The system of claim 2, wherein said spring is adjustable to alter the resistance of the one-way valve to opening.

4. A gas delivery system, comprising:
   an oxygen source;
   a housing having an inlet, a first outlet, a second outlet and a third outlet, said housing including a valve that defines a first volume within said housing between the valve and the mouthpiece and a second volume between the valve and inlet, wherein said valve rests on a valve seat that is angled with respect to a longitudinal axis of said housing;
   a patient interface associated with said first outlet of said housing, said valve being selectively openable when a patient inhales through said patient interface;
   a nebulizer associated said inlet of said housing;
   an oxygen supply line associated with said nebulizer and said oxygen source;
   a filter mechanism associated with said second outlet of said housing;
   a reservoir associated with said third outlet of said housing; and
   wherein said housing receives a mixture of oxygen and medicine from said nebulizer that is directed to said reservoir, the mixture inflating said reservoir until said valve is opened, thereby allowing the mixture from said nebulizer and said reservoir to exit a first opening.

5. The gas delivery system of claim 4, wherein said patient interface is at least one of a mouth piece or a mask.

6. The gas delivery system of claim 4, wherein said reservoir is rigid.

7. The gas delivery system of claim 6, wherein said reservoir further comprises a valve.

8. A method of supplying oxygen to a patient comprising:
   providing an oxygen source;
   providing a housing having an inlet, a first outlet, a second outlet and a third outlet, said housing including a valve that defines a first volume within said housing between the valve and the mouthpiece and a second volume between the valve and inlet;
   providing a mouthpiece associated with said first outlet of said housing, said valve being selectively openable when a patient inhales through said mouth piece;
   providing a reservoir associated with said third outlet of said housing, said reservoir having a second valve;

directing oxygen from said oxygen source to said housing;
directing said oxygen to said reservoir;
opening said valve when said patient inhales;
opening said second valve when said oxygen in said reservoir is depleted;
closing said first valve and said second valve when said patient is not inhaling.

9. The method of claim 8, further comprising providing a nebulizer associated said inlet of said housing wherein said reservoir receives a mixture of oxygen and medicine.

* * * * *